United States Patent [19]

Tantram

[11] 3,960,495

[45] June 1, 1976

[54] DETECTION OF COMBUSTIBLE GASES

[76] Inventor: Anthony Desmond Shand Tantram, 50 Downs Way, Great Bookham, near Leatherhead, Surrey, England

[22] Filed: Feb. 21, 1975

[21] Appl. No.: 551,849

Related U.S. Application Data

[63] Continuation-in-part of Ser. No. 330,454, Feb. 7, 1973, abandoned.

[30] Foreign Application Priority Data

Feb. 15, 1972 United Kingdom................ 7035/72
July 26, 1972 United Kingdom.............. 35050/72

[52] U.S. Cl........................... 23/232 E; 23/230 PC; 23/232 R; 23/254 R; 23/254 E; 73/27 R
[51] Int. Cl.²................. G01N 27/16; G01N 31/10; G01N 31/12
[58] Field of Search........ 23/232 R, 232 E, 230 PC, 23/253 PC, 254 R, 254 E; 73/27 R

[56] References Cited
UNITED STATES PATENTS

| | | |
|---|---|---|
| 2,768,069 | 10/1956 | Thompson................. 23/232 E UX |
| 2,876,064 | 3/1959 | Yant et al. .................... 23/254 E X |
| 3,607,084 | 9/1971 | Mackey et al.................... 23/232 E |
| 3,725,005 | 4/1973 | Innes................................. 23/232 E |
| 3,771,960 | 11/1973 | Kim et al.......................... 23/232 E |

OTHER PUBLICATIONS

The Estimation of Firedamp:Applications & Limitations of the Pellistor, Baker et al., The Mining Engineer, Jan. 69, pp. 237–244.

*Primary Examiner*—Morris O. Wolk
*Assistant Examiner*—Michael S. Marcus
*Attorney, Agent, or Firm*—Haseltine, Lake & Waters

[57] ABSTRACT

Method of continuously monitoring an atmosphere to detect the presence of a combustible gas or vapor in the atmosphere which comprises testing the atmosphere with a detector including a transducer which responds to the presence of the combustible gas or vapor and continuously supplying to the vicinity of the transducer a controlled small amount of a combustible gas or vapor to which the transducer responds so that the detector normally indicates the presence of at least the said controlled small amount of combustible gas or vapor, inoperativeness of the detector owing, e.g. to malfunctioning of the transducer being observable by the detector ceasing to indicate the presence of at least the said controlled small amount of combustible gas or vapor.

7 Claims, 1 Drawing Figure

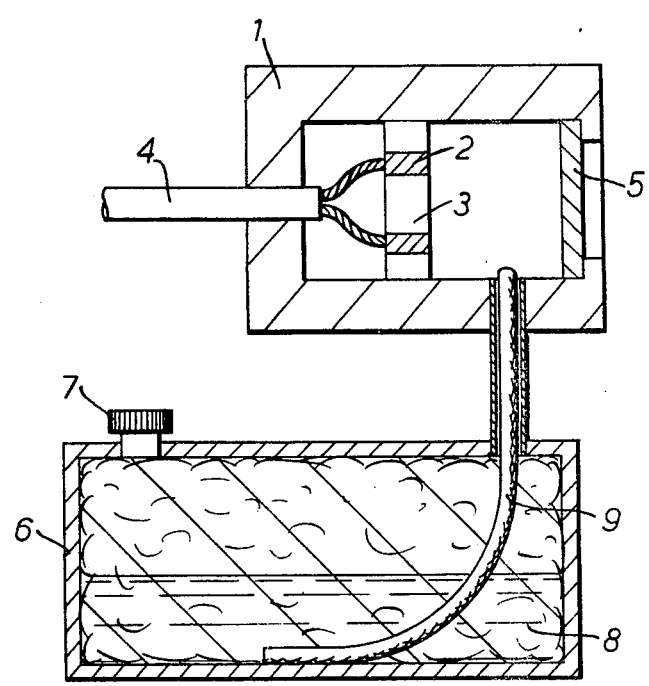

DETECTION OF COMBUSTIBLE GASES

This invention is a continuation-in-part of my application Ser. No. 330,454 filed on 7th February 1973 and now abandoned.

BACKGROUND OF THE INVENTION

This invention relates to the continuous monitoring of an atmosphere to detect the presence of combustible gas or vapour, for example the presence of methane in coal mines.

Methane is the major flammable component of fire damp in coal mines and for reasons of safety it is necessary to measure quantitatively the presence of methane in coal mines, to record the concentration of methane and/or to set off an alarm when the concentration reaches a predetermined level. Methane concentration has been measured by means of detectors which include a catalyst for the oxidation of methane. Methane and air react on the surface of the catalyst. The heat evolved from this reaction is measured and can be used to provide a measure of the amount of methane present. Such detectors normally require a transducer which performs three functions: (1) it acts as a catalyst for the oxidation of methane; (2) it acts as a heater to raise the catalyst to the temperature at which it will catalyse the oxidation reaction; and (3) it acts as means for sensing the heat evolved in the oxidation reaction. In some detectors these three functions are performed by the same item, for example a coil of platinum wire which is part of a resistance bridge and through which a current is normally passed. The passage of the current heats the coil of platinum wire to a temperature at which it will catalyse the reaction between methane and oxygen. The heat evolved during the reaction further heats the coil of platinum wire and thereby increases its resistance, which is detected by means of the resistance bridge. Such detectors are described in an article in "The Mining Engineer", January 1969, pgs. 237 to 244.

Methane concentration can also be measured by means of a semiconductor transducer whose resistance varies with the concentration of flammable gas. Such semiconductor transducers and their use in detectors for flammable gas are described, for example, in U.S. Pat. Nos. 3,603,954 and 3,631,436.

A problem which arises when using such detectors is that they are rendered inoperative if the transducer becomes inactive, for instance in the case of a catalytic transducer as a consequence of poisoning or inhibition. There are usually present in a mine substances which, if they come into contact with the catalyst, will reduce the efficiency of the catalyst or render it useless. A detector containing an inoperative transducer, for example a poisoned catalyst, will give a reading indicating the presence of no methane regardless of whether methane is present or not and it is not possible to tell without carrying out tests on the detector whether it is malfunctioning or not.

SUMMARY OF THE INVENTION

According to the present invention there is provided a method of continuously monitoring an atmosphere to detect the presence of a combustible gas or vapour in the atmosphere which method comprises testing the atmosphere with a detector including a transducer which responds to the presence of the combustible gas or vapour and continuously supplying to the vicinity of the transducer a controlled small amount of a combustible gas or vapour to which the transducer responds so that the detector normally indicates the presence of at least the said controlled small amount of combustible gas or vapour, inoperativeness of the detector owing, e.g. to malfunctioning of the transducer being observable by the detector ceasing to indicate the presence of at least the said controlled small amount of combustible gas or vapour.

Preferably the detector is a catalytic one having a catalyst for the oxidation of the combustible gas or vapour. The catalytic detector can include two heat sensing elements which are part of a resistance bridge, the catalyst being supported on one of the heat sensing elements.

BRIEF DESCRIPTION OF THE DRAWING

The accompanying drawing is a sectional elevational view showing a catalytic detector for use in monitoring an atmosphere to detect the presence of a combustible gas or vapour, in accordance with the invention.

DESCRIPTION OF THE PREFERRED EMBODIMENTS

The preferred detector is a catalytic detector in which the transducer includes a catalyst for the oxidation of combustible gas or vapour. The invention is further described with reference to the use of a catalytic detector and to the detection of methane but the invention is not confined to the use of a catalytic detector and the detection of methane.

In one embodiment of the invention, the means continuously to provide the controlled small amount of combustible gas or vapour is a substance which will continuously emit a combustible gas or vapour. The substance is placed in the vicinity of the catalyst of the catalytic detector. The emitting substance can be substance which gives off a combustible gas or vapour by evaporation under the conditions in which the detector is used so that the air becomes saturated with the gas or vapour. The composition of the mixture of air and combustible gas or vapour will be known from a knowledge of the ambient temperature and the vapour pressure of the emitting substance at that temperature. The lower limit of the amount of gas or vapour which should be present in the vicinity of the catalyst depends upon the sensitivity of the catalytic detector. The upper limit of the amount of gas or vapour which should be present is determined by the need to have sufficient oxygen present to combust both the gas or vapour provided to check the catalytic detector and the gas whose presence is to be detected at its highest concentration. For example, suppose that the gas whose presence is to be detected is methane, in concentrations up to 4% by volume. When methane is oxidised by air in the presence of a catalyst, if the concentration of methane rises above 9% by volume the rate of reaction, and hence the heat evolved, are limited by lack of sufficient oxygen to react with all the methane present. In order that the amount of oxidisable reactant, i.e. methane plus the gas or vapour from the emitting substance, does not exceed that amount which can be combusted by air without lack of oxygen limiting the rate of reaction the oxygen requirement of the amount of combustible gas or vapour deliberately supplied should not exceed the oxygen requirement of 5% by volume of methane. The small controlled amount of combustible gas or vapour supplied to the vicinity of the transducer can be selected to be any amount which is sufficient to be detected and which does not exceed the oxygen requirement of 5% by volume of methane. For example, the controlled amount of combustible gas or vapour can have an oxygen requirement equivalent to that of 1, 2, 3, 4 or 5% of methane. The amount of gas or vapour whose oxygen requirement is equal to that of, say, 5% by volume of methane can be calculated from known data for particular compounds. The amount of gas or vapour from the emitting substance in the vicinity of the catalyst at a particular temperature will depend upon the vapour pressure of the emitting substance at the particular temperature. When methane is the gas to be detected the emitting substance is preferably a compound whose vapour pressure at ambient temperature is in the range of from 0.03 mm of mercury to 6 mm of mercury at 20°C; a compound whose vapour pressure is in the range of from 0.3 mm of mercury to 3 mm of mercury is particularly preferred. Suitable compounds are organic chemical compounds consisting largely or entirely of carbon and hydrogen whose molecular weights range from 70 to 190 and the compound should have a heat of combustion about 2 to 8 times that of methane. As examples of compounds which can be used as emitting substance there are mentioned cis- and trans-decalin, naphthalene camphor, diacetone alcohol, amylalcohol 1-hexanol, dipropyl ketone, methylamyl ketone, furfuraldehyde, isobutyric acid, decane, hendecane, phenetole and benzaldehyde.

It will be appreciated that the emitting substance will be consumed over a period of time by operation of the catalytic detector. Hence it will be necessary periodically to examine and if necessary replace the emitting substance. If at the time the emitting substance is consumed the concentration of the gas or vapour to be detected is zero, the catalytic detector will give a zero reading, i.e. a reading indicating the presence of no combustible gas, and would thereby draw attention to itself. An alarm can be provided to draw attention to the fact that the detector is giving a zero reading. In any event, it is possible to determine by calculation and experience approximately how long a particular amount of emitting substance should last in a particular environment and to examine the catalytic detector in good time before the expiry of this period.

The vapour pressure of substances varies markedly with temperature and consequently if the emitting substance operates by evaporation and the catalytic detector is in an environment where marked temperature changes could occur it will normally be necessary to compensate for the consequent change in vapour pressure, otherwise the operation of the catalytic detector could be upset. Such compensation can be achieved in a number of ways and if an emitting substance of low vapour pressure is used with a very sensitive catalytic detector no such compensation may be required. As stated above, the catalytic detector normally includes one arm of a resistance bridge. In order that only temperature changes due to the oxidation of gases shall be detected, another arm of the bridge is normally situated in the same environment as the first arm and is identical to the first arm apart from the absence of a catalyst. In order to compensate for changes in ambient temperature it is possible to couple to the resistance bridge a temperature compensator so that it automatically adjusts the alarm level of the catalytic detector. Another method of compensating for ambient temperature changes is to have a calibration chart for the vapour pressure of the gas or vapour emitted from the substance as a function of ambient temperature and reset the zero of the catalytic detector by means of the calibration chart. To avoid the need for temperature compensation, the catalytic detector can be contained in a thermostat. The catalytic detector can be used for spot checks where the temperature is measured at the time of the check and the emitting substance is in a valved container and admitted to the proximity of the catalyst only for the spot check. In one embodiment the catalytic detector includes a closed vessel containing only liquid and vapour from the liquid. A pressure transducer is situated in one wall of the vessel. As the temperature varies the pressure inside the vessel will vary. This variation can be observed by means of the pressure transducer and used to compensate automatically for the temperature variation. The liquid in the vessel can be chosen to have a temperature coefficient of vapour pressure substantially the same as that of the emitting substances.

In one embodiment of the invention the means continuously to provide a mixture of air and combustible gas or vapour is an emitting substance which emits a gas or vapour not by evaporation but by chemical decomposition.

The emitting substance can be a liquid contained in a vessel, the liquid being supplied to the vicinity of the catalyst of the catalytic detector via a wick extending from the vessel. Liquid then evaporates from the wick.

In a preferred embodiment of the invention, combustible gas or vapour is supplied to the vicinity of the catalyst by evaporation of solvent from a solution containing excess solute. The presence of a solute in a solvent will reduce the vapour pressure of the solvent. As the temperature increases, the solubility of a solid or liquid solute in a solvent will increase. As the ambient temperature rises, the vapour pressure of the solvent will tend to increase but this effect will be opposed because the amount of solute dissolved in the solvent will also increase with temperature. Hence the depressive effect of the solute on the vapour pressure of the solvent will increase with temperature. The net result will be that the variation of the vapour pressure of the solvent with temperature will be less steep than would be the case if no solute were present. It will be appreciated that the solute should have a low vapour pressure, negligible in comparison with that of the solvent. By using a solution containing excess solute in accordance with the invention, it is possible to reduce by factor of about 3 the coefficient of vapour pressure with temperature of a solvent. Hence the sensitivity to ambient temperature of the catalytic detector is reduced. This means that simpler, cheaper temperature compensation for the catalytic detector can be used, or in some cases the need for further temperature compensation may be eliminated.

The solution can comprise a liquid solvent and a solid solute, two partially miscible liquids or two solids which form a solid solution. It is also possible to use a solvent or a solute which comprises two or more components. If the solute is multi-component, the components must have closely matching vapour pressure and temperature coefficients, otherwise the more volatile will tend to evaporate preferentially, thus changing the composition and vapour pressure. By varying the constituents and amount of components in a solute and/or a solvent, it may be possible to achieve a better overall control of the temperature coefficient. Also, the solute or the solvent may be a commercially available material that is a mixture anyway, for example, a petroleum fraction or a paraffin wax.

Where the solvent-solute combination contains a liquid, the liquid may be immobilised in an inert porous support of some kind, for example, a bed of porous granules. This also permits air to be drawn through the inert porous support, if necessary.

The solute and solvent are selected, bearing in mind the requirements of the catalytic detector, from appropriate data on solubilities and vapour pressures in the literature and reference books and making use of the relevant laws of physical chemistry, such as Raoult's law. For the maximum effect the solute should have a high solubility in the solvent at the upper end of the range of ambient temperature in which the detector is to operate. Preferred materials are combinations of solute and solvent of similar chemical nature and solutes having a melting point not far above the upper limit of ambient temperature in which the catalytic detector is to operate.

The following are examples of suitable solutions:

| Solvent | Solute |
| --- | --- |
| iso-butyric acid | capric acid |
| amyl alcohol | tri-decyl alcohol |
| decane | nona-decane |
| propionic acid | lauric acid |
| propionic acid | capric acid |
| n-butyl alcohol | ethyl carbamate |
| n-butyl alcohol | cyanamid |

In another embodiment the mixture of air and combustible gas or vapour can be provided from a gas cylinder containing a mixture of air and combustible gas or vapour of a suitable known composition. In operation the mixture is passed from the gas cylinder to the vicinity of the catalyst via a conduit and if the conduit is provided with a constant flow valve or meter the rate at which the mixture is passed to the vicinity of the catalyst will be independent of the ambient temperature. Hence the gas detector will not require to be compensated for changes in ambient temperature.

When a catalytic detector is used to measure the amount of methane present in a mine, the transducer is usually contained in a vessel which separates the transducer from the general mine atmosphere. Air and any methane enter the vessel after passage through active carbon filters and/or sintered metal, e.g. bronze, discs. The filters and sintered discs serve to remove dust particles and catalyst poisons from the air before it comes into contact with the catalyst and to reduce or eliminate the effect on the catalyst of the rate of flow of air in the mine. Catalytic detectors whose catalysts are contained in such a vessel are described in the article in "The Mining Engineer" referred to above. In accordance with the invention, when the catalyst of a catalytic detector is contained in such a vessel the emitting substance is preferably also contained in the vessel.

In a particular embodiment of the present invention, the catalytic detector comprises a housing 1. Inside the housing is a heat sensing means 2 including a catalyst for the oxidation of flammable gas. Also present in the housing 1 is a heat sensing means 3 which is identical with heat sensing means 2, except that it does not include a catalyst for the oxidation of flammable gas. The two heat sensing means 2 and 3 are connected by a cable 4 to a conventional resistance bridge which is not illustrated. The housing 1 includes a sintered metal disc 5. When the detector is in use it is placed in the atmosphere to be monitored and gas from that atmosphere enters the housing through the sintered metal disc 5.

Adjacent to the housing 1 is a vessel 6 having a filler cap 7 and containing a liquid 8 which will undergo evaporation under the ambient conditions to provide a flammable gas or vapour. A wick 9 extends from the interior of the vessel to the interior of the housing 1. Liquid from the vessel travels via the wick into the housing 1, where it evaporates. The evaporation takes place in accordance with well known laws of physical chemistry, so that the amount of flammable gas provided via the wick is known and can be determined to be equivalent to, for example 2% methane. Hence an operator using the detector to monitor an atmosphere will expect the detector to indicate the presence of at least 2% of methane; if the detector indicates the presence of less than 2% methane then the operator will suspect that the catalyst on the heat sensing means 2 is poisoned and he will be alerted to investigate.

The gas detector of the invention has been described with particular reference to the detection of methane in coal mines but it will be appreciated that there are numerous applications for the gas detector. Thus the gas detector can be used to detect petrol vapour on car ferries, it can be used to test for gas leaks with both town and natural gas, it can be used to detect flammable gases in oil tankers and in chemical plants. Numerous applications will occur to those skilled in the art.

I claim:

1. In a method of continuously monitoring an atmosphere to detect the presence of a combustible gas or vapour in the atmosphere comprising testing the atmosphere with a detector including a transducer which responds to the presence of the combustible gas or vapour in the atmosphere, the improvement comprising the steps of continuously supplying to the vicinity of the transducer a controlled known small amount of a known combustible gas or vapour to which the transducer responds so that the detector normally indicates the presence of at least the said controlled amount of combustible gas or vapour, said detector indicating malfunctioning of said transducer by not giving a reading for the known combustible gas or vapor.

2. A method according to claim 1 wherein the said controlled known small amount of known combustible gas or vapour is provided by a substance which will continuously emit by evaporation the combustible gas or vapour, the substance having a vapour pressure at 20°C. in the range of from 0.03 mm to 6 mm of mercury, being composed largely or entirely of carbon and hydrogen and having a molecular weight in the range of from 70 to 190.

3. A method according to claim 1 wherein the said controlled known small amount of known combustible gas or vapour is provided by a substance which will continuously emit by evaporation the combustible gas or vapour, the substance being selected from the group consisting of cis- and trans-decalin, naphthalene, camphor, diacetone alcohol, amylalcohol, 1-hexanol, dipropyl ketone, methylamyl ketone, furfuraldehyde, isobutyric acid, decane, hendecane, phenetole and benzaldehyde.

4. A method according to claim 1 wherein the said controlled known small amount of known combustible gas or vapour is provided by evaporation of a solvent from a solution containing excess solute.

5. A method according to claim 4 wherein the solution is a solution of isobutyric acid and capric acid, amyl alcohol and tridecyl alcohol, decane and monadecane, propionic acid and lauric acid, propionic acid and capric acid, n-butyl alcohol and ethyl carbamate or n-butyl alcohol and cyanamid.

6. In a method of continuously monitoring an atmosphere to detect the presence of a combustible gas or vapour present in the atmosphere comprising the steps of continuously testing the atmosphere with a catalytic detector, said catalytic detector including a catalyst for the oxidation of a combustible gas or vapour and heat sensing means for sensing heat of combustion when combustible gas or vapour is present and is combusted in the presence of the catalyst; the improvement comprising continuously supplying to the vicinity of said catalyst, in addition to the atmosphere being monitored, a controlled substantially known small amount of a known combustible gas or vapour thus forming at said vicinity a mixture of said atmosphere and said known combustible gas or vapour and then combusting said mixture so that the detector normally indicates at least the presence of said controlled known amount of known combustible gas or vapour, said detector indicating poisoning of said catalyst by not giving a reading for the known presence of the combustible mixture.

7. A method according to claim 6 wherein the combustible gas or vapour to be detected is methane and said controlled known small amount of known combustible gas or vapour has the same oxygen requirement for complete combustion as said atmosphere containing 2% by volume of methane.

* * * * *